United States Patent
Lee et al.

(10) Patent No.: US 8,351,051 B2
(45) Date of Patent: Jan. 8, 2013

(54) SYSTEM AND METHOD OF MEASURING IRREGULARITY OF A GLASS SUBSTRATE

(75) Inventors: Soon-Jong Lee, Seoul (KR); Bong-Joo Woo, Suwon (KR); Byoung-Chan Park, Gyeonggi-Do (KR); Seong-Jin Choi, Gyeonggi-Do (KR); Jae-Hoon Chung, Gyeonggi-Do (KR)

(73) Assignee: Semisysco Co., Ltd., Suwon, Gyeonggi-Do (KR)

( * ) Notice: Subject to any disclaimer, the term of this patent is extended or adjusted under 35 U.S.C. 154(b) by 30 days.

(21) Appl. No.: 13/094,711

(22) Filed: Apr. 26, 2011

(65) Prior Publication Data

US 2012/0133952 A1    May 31, 2012

Related U.S. Application Data

(63) Continuation of application No. PCT/KR2011/001340, filed on Feb. 25, 2011.

(30) Foreign Application Priority Data

Nov. 25, 2010 (KR) .......................... 10-2010-0118236

(51) Int. Cl.
*G01B 11/30* (2006.01)
*G01N 21/00* (2006.01)
(52) U.S. Cl. .................. 356/600; 356/239.1; 356/237.2
(58) Field of Classification Search ..... 356/239.1–239.8
See application file for complete search history.

(56) References Cited

U.S. PATENT DOCUMENTS

| | | | | | |
|---|---|---|---|---|---|
| 3,989,387 | A | * | 11/1976 | Hategan | 356/239.1 |
| 6,144,446 | A | * | 11/2000 | Nagasaki et al. | 356/237.3 |
| 6,433,353 | B2 | * | 8/2002 | Okugawa | 250/559.4 |
| 7,420,671 | B2 | * | 9/2008 | Sonda | 356/239.1 |
| 2007/0216897 | A1 | * | 9/2007 | Sonda | 356/239.1 |

FOREIGN PATENT DOCUMENTS

| | | |
|---|---|---|
| JP | 2000-146554 A | 5/2000 |
| KR | 2007-0019984 A | 2/2007 |

* cited by examiner

*Primary Examiner* — Michael P Stafira
(74) *Attorney, Agent, or Firm* — Edwards Wildman Palmer LLP

(57) ABSTRACT

A system and a method of measuring irregularity of a glass substrate using only a reflection light reflected by an upper surface of reflection lights reflected by the upper surface and a lower surface of the glass substrate are disclosed. The system includes a light source section configured to output a first light to the glass substrate and a screen. Here, the first light outputted from the light source section is reflected by an upper surface and a lower surface of the glass substrate, a first reflection light reflected by the upper surface of the glass substrate is inputted into the screen, a first line is formed on the screen in accordance with the input of the first reflection light, a second reflection light reflected by the lower surface of the glass substrate is inputted into the screen through the upper surface, a second line is formed on the screen in accordance with the input of the second reflection light, and the light source section and the screen are disposed on the basis of the glass substrate so that the lines are separated.

18 Claims, 7 Drawing Sheets

(A)

(B)

SYSTEM AND METHOD OF MEASURING IRREGULARITY OF A GLASS SUBSTRATE

CROSS REFERENCE TO RELATED APPLICATIONS

This application is a continuation of PCT International Application No.: PCT/KR2011/001340, filed Feb. 25, 2011, which claims the benefit of Korean Patent Application 10-2010-0118236, filed Nov. 25, 2010, the contents of which are incorporated herein in their entireties by reference.

TECHNICAL FIELD

Example embodiment of the present invention relates to a system and a method of measuring irregularity (non-uniformity) of a glass substrate by inputting a light having specific wavelength to the glass substrate.

RELATED ART

Surface of a glass substrate employed in a display device, e.g. liquid crystal display LCD may not be uniform due to defect, etc.

In case that the display device employs the glass substrate having non-uniform surface, the display device may not realize desired performance due to the irregularity of the glass substrate. As a result, the display device may be discarded, and so yield of the display device may be lowered.

Accordingly, it is important to detect in advance the glass substrate having defect by measuring irregularity of the glass substrate before performing other process after manufacturing the glass substrate.

Hereinafter, a process of manufacturing the glass substrate and a method of measuring irregularity of the glass substrate will be described in detail.

FIG. 1 is a view illustrating a common process of manufacturing a glass substrate.

As shown in FIG. 1, liquefied glass solution is injected into a furnace. In this case, the injected glass solution flows in an arrow direction, and so the glass substrate is manufactured.

However, curve lines may occur in a flowing direction of the glass solution while the glass solution is flowing, and thus the glass substrate having non-uniform surface may be manufactured.

Accordingly, to detect the glass substrate having non-uniform surface, various methods of measuring irregularity of the glass substrate have been developed.

The first method measures irregularity of the glass substrate by irradiating a light having specific wavelength to the glass substrate under the condition of floating the glass substrate on water.

The second method measures irregularity of the glass substrate by irradiating a light having specific wavelength to the glass substrate under the condition of attaching a paper on a lower surface of the glass substrate.

The third method measures irregularity of the glass substrate by irradiating a light having specific wavelength to the glass substrate under the condition of coating certain substance on a lower surface of the glass substrate.

The above methods process the lower surface of the glass substrate so as to remove a light, not needed for measuring the irregularity, reflected by the lower surface of the glass substrate of lights reflected by the glass substrate.

However, the methods require further processes such as a process of coating the substance on the lower surface of the glass substrate and a process of removing the substance coated on the lower surface after the measuring of the irregularity is finished, etc., and thus time and cost taken for measuring the irregularity may increase.

Additionally, it is difficult to remove completely the light reflected by the lower surface of the glass substrate though the lower surface of the glass substrate is processed. Accordingly, it is not easy to measure accurately the irregularity of the glass substrate.

Furthermore, it is difficult to automate the process of measuring the irregularity of the glass substrate due to the processing of the lower surface of the glass substrate.

DISCLOSURE

Technical Problem

Example embodiment of the present invention provides a system and a method of measuring irregularity of a glass substrate without performing any process to a lower surface of the glass substrate.

Another example embodiment of the present invention provides a system and a method of measuring irregularity of a glass substrate using only a reflection light reflected by an upper surface of reflection lights reflected by the upper surface and a lower surface of the glass substrate.

Technical Solution

In one aspect, the present invention provides a system for measuring irregularity of a glass substrate comprising: a light source section configured to output a first light to the glass substrate; and a screen. Here, the first light outputted from the light source section is reflected by an upper surface and a lower surface of the glass substrate, a first reflection light reflected by the upper surface of the glass substrate is inputted into the screen, a first line is formed on the screen in accordance with the input of the first reflection light, a second reflection light reflected by the lower surface of the glass substrate is inputted into the screen through the upper surface, a second line is formed on the screen in accordance with the input of the second reflection light, and the light source section and the screen are disposed on the basis of the glass substrate so that the lines are separated.

The system further includes a sensing section configured to sense the lines formed on the screen; and an irregularity measuring section configured to extract only the first line of the lines sensed by the sensing section, and measure irregularity of the glass substrate by analyzing the extracted first line.

The light source section includes a light source configured to output a second light; a first lens configured to diffuse the second light outputted from the light source; and a second lens configured to change the second light diffused by the first lens into the first light having constant beam width.

The light source, the first lens and the second lens are included in one case, and the case moves omnidirectionally. Here, the system detects optimal location at which the lines are separated through a method of moving the case under the condition of fixing the glass substrate and the screen, and fixes the case at the detected location.

Ratio of distance between the light source section and the glass substrate and distance to a part on which the first line is formed of the screen from the glass substrate is approximately 1:1 to approximately 1:0.5 and the light source section locates in the range of about 45° to about 80° on the basis of the glass substrate.

The lines are separated in case that distance to a part on which the first line is formed of the screen from the glass substrate is less than approximately 60 mm under the condition that distance between the light source section and the glass substrate is about 60 mm to about 120 mm and the light source section locates in the range of approximately 45° to approximately 80° on the basis of the glass substrate.

Distance between the glass substrate and the screen decreases according as angle between the glass substrate and the light source section increases under the condition that distance between the second lens and the glass substrate fixes.

In another aspect, the present invention provides a system for measuring irregularity of a glass substrate comprising: a light source configured to output a light; and a slit section configured to have at least one slit. Here, the light outputted from the light source is inputted into the glass substrate through the slit of the slit section, the inputted light is reflected by an upper surface and a lower surface of the glass substrate, and a first line corresponding to a first reflection light reflected by the upper surface of the glass substrate is separated from a second line corresponding to a second reflection light reflected by the lower surface of the glass substrate.

The system further includes a sensing section configured to sense the first line and the second line; and an irregularity measuring section configured to extract only the first line of the lines sensed by the sensing section, and measure irregularity of the glass substrate by analyzing the extracted first line. Here, the sensing section senses the lines by taking directly the glass substrate.

The system further includes a screen in which the first reflection light and the second reflection light are inputted; a sensing section; and an irregularity measuring section. Here, the first line corresponding to the first reflection light and the second line corresponding to the second reflection light are formed on the screen, the sensing section senses the lines, and the irregularity measuring section measures irregularity of the glass substrate by extracting and analyzing only the first line of the lines sensed by the sensing section.

In still another aspect, the present invention provides a method of measuring irregularity of a glass substrate, the method comprising: inputting a first light into the glass substrate; and sensing at least one of a first line corresponding to a first reflection light reflected by an upper surface of the glass substrate and a second line corresponding to a second reflection light reflected by a lower surface of the glass substrate, the second reflection light being outputted through the upper surface. Here, the first line and the second line are separated.

The method further includes extracting only the first line from the lines; and measuring irregularity of the glass substrate by analyzing the extracted first line.

The step of inputting the first light into the glass substrate includes diffusing a second light using a first lens; and changing the diffused second light into the first light having constant beam width using a second lens, and inputting the first light into the glass substrate. Here, the first line is formed on a screen by the first reflection light reflected by the upper surface of the glass substrate, and the second line is formed on the screen by the second reflection light reflected by the lower surface of the glass substrate.

The light source, the first lens and the second lens are included in one case, the case moves omnidirectionally. The method further includes moving the case until the lines are separated under the condition of fixing the glass substrate and the screen; and fixing the case after the lines are separated. Here, the irregularity of the glass substrate is measured under the condition that the light source and the screen are fixed.

Ratio of distance between the second lens and the glass substrate and distance to a part on which the first line is formed of the screen from the glass substrate is approximately 1:1 to approximately 1:0.5 and the light source locates in the range of about 45° to about 80° on the basis of the upper surface of the glass substrate.

The lines are separated in case that distance to a part on which the first line is formed of the screen from the glass substrate is less than approximately 60 mm under the condition that distance between the second lens and the glass substrate is about 60 mm to about 120 mm and the light source locates in the range of approximately 45° to approximately 80° on the basis of the upper surface of the glass substrate.

The step of sensing includes sensing the first line and the second line by taking directly the glass substrate. Here, the first light is inputted into the glass substrate through a slit section having at least one slit.

The first reflection light is inputted to a screen, the first line is formed on the screen by the first reflection light, the second reflection light is inputted to the screen, and the second line is formed on the screen by the second reflection light. Here, the first light is inputted to the glass substrate through a slit section having at least one slit.

Advantageous Effects

A system and a method of measuring irregularity of a glass substrate of the present invention measure irregularity of the glass substrate without performing any process to a lower surface of the glass substrate, and thus time and cost taken for measuring the irregularity may decrease. It is also easy to automate the measuring process.

Additionally, the system and the method analyzes a first line after separating clearly the first line corresponding to a first reflection light reflected by an upper surface of the glass substrate from a second line corresponding to a second reflection light reflected by a lower surface of the glass substrate, and so the system and the method may measure accurately irregularity of the glass substrate.

Furthermore, since the system is embodied with simple elements, it is easy to realize the system and error of the system may be reduced.

BRIEF DESCRIPTION OF DRAWINGS

Example embodiments of the present invention will become more apparent by describing in detail example embodiments of the present invention with reference to the accompanying drawings, in which.

| | |
|---|---|
| 200: glass substrate | 200a: upper surface |
| 200b: lower surface | 300: light source section |
| 302: screen | 310: first line |
| 312: second line | 400: sensing section |
| 402: irregularity measuring section | 410: irregularity determining section |
| 500: light source | 502: first lens |
| 504: second lens | 700: light source |
| 702: glass substrate | 704: slit section |
| 706: sensing section | 1000: light source |
| 1002: glass substrate | 1004: slit section |
| 1006: screen | 1008: sensing section |

DETAILED DESCRIPTION

Hereinafter, embodiments of the present invention will be described in detail with reference to accompanying drawings.

Figure 1:
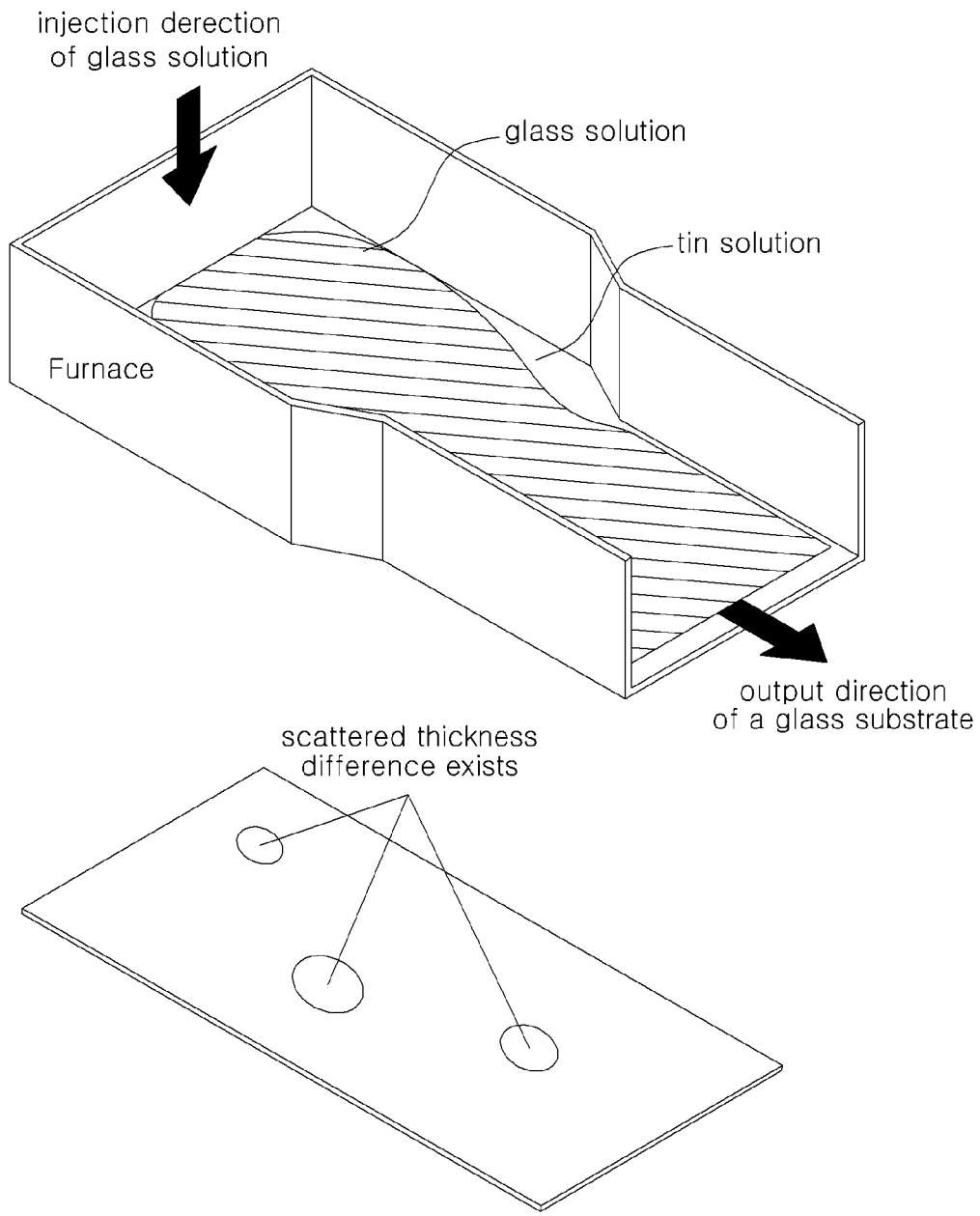
FIG. 1 is a view illustrating a common process of manufacturing a glass substrate.
Figure 2:
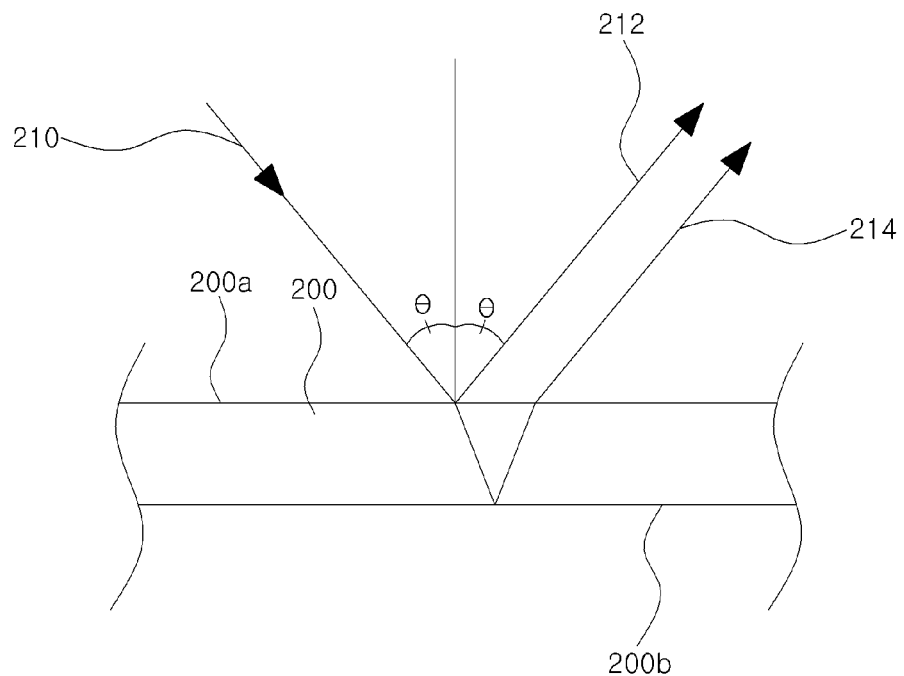
FIG. 2 is a sectional view illustrating reflection by a glass substrate according to one example embodiment of the present invention.

FIG. 2 is a sectional view illustrating reflection by a glass substrate according to one example embodiment of the present invention.

A system for measuring irregularity of a glass substrate of the present embodiment measures irregularity (non-uniformity) of a surface of a glass substrate 200, preferably irregularity of an upper surface 200a of the glass substrate 200. Here, the glass substrate 200 is a transparent substrate employed in a display device, e.g. a base substrate employed in a liquid crystal display LCD.

Hereinafter, light reflection characteristics of the glass substrate 200 will be described, and then the system for measuring irregularity of the glass substrate 200 will be described in detail.

Firstly, the light reflection characteristics of the glass substrate 200 will be described in detail.

Referring to FIG. 2, in case that a light 210 having specific wavelength outputted from a light source (not shown) is inputted into the glass substrate 200, a part of the inputted light 200 is reflected by the upper surface 200a of the glass substrate 200, the other light is reflected by a lower surface 200b of the glass substrate 200. As a result, in case that the light 210 is inputted into the glass substrate 200, a first reflection light 212 is generated by the upper surface 200a and a second reflection light 214 is generated by the lower surface 200b, the second reflection light 214 being outputted through the upper surface 200a.

Generally, in case that the upper surface 200a and the lower surface 200b of the glass substrate 200 are uniform, a part of the light 210 is reflected by the upper surface 200a, an input angle θ being identical to a reflection angle θ. Additionally, the second reflection light 214 reflected by the lower surface 200b propagates in parallel to the first reflection light 212.

Phenomenon when the upper surface 200a or the lower surface 200b is non-uniform is not the same as that when the upper surface 200a and the lower surface 200b is uniform. However, the first reflection light 212 and the second reflection light 214 are generated by the upper surface 200a and the lower surface 200b of the glass substrate 200.

Since layers are usually laminated on the upper surface 200a of the glass substrate 200 through a sputtering method in a process of manufacturing the display device, it is important to measure irregularity of the upper surface 200a of the glass substrate 200.

However, since the second reflection light 214 reflected by the lower surface 200b as well as the first reflection light 212 reflected by the upper surface 200a generates when the light 210 is inputted into the glass substrate 200, it is difficult to measure irregularity of the upper surface 200a. Specially, it is difficult to separate only the first reflection light 212 because the second reflection light 214 interferes with the first reflection light 212.

Accordingly, the present invention provides a method of preventing interference of the second reflection light 214 under the condition that the reflection light 212 and the second reflection light 214 generate.

Hereinafter, the system and a method of measuring irregularity of the glass substrate 200 will be described in detail with reference to accompanying drawings.

Figure 3:
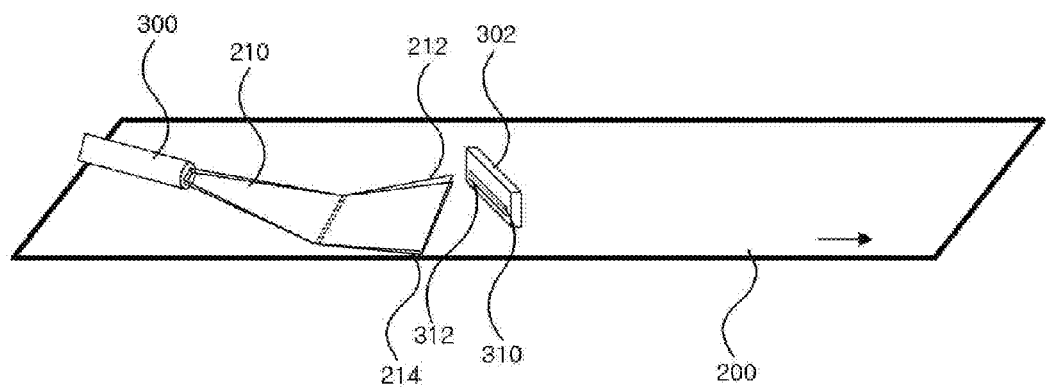
FIG. 3 is a view illustrating schematically a system for measuring irregularity of a glass substrate according to a first embodiment of the present invention.

FIG. 3 is a view illustrating schematically a system for measuring irregularity of a glass substrate according to a first embodiment of the present invention.

In FIG. 3, a light 210 having specific wavelength outputted from a light source section 300 is inputted into the glass substrate 200, and thus the first reflection light 212 and the second reflection light 214 are outputted reflected by the upper surface 200a and the lower surface 200b of the glass substrate 200. Here, the light 210 may have constant beam width, and be visible ray, ultraviolet ray or infrared ray.

In one embodiment of the present invention, the light source section 300 may output the light 210 using a laser, or output the light 210 having constant beam width using a lens as described below.

The first reflection light 212 and the second reflection light 214 reflected by the glass substrate 200 are inputted into a screen 302 located on the glass substrate 200. Here, the screen 302 is made up of opaque substance, and so a first line 310 as interference fringe corresponding to the first reflection light 212 and a second line 312 as interference fringe corresponding to the second reflection light 214 are formed on the screen 302.

On the other hand, the system of the present embodiment disposes its elements so that the first line 310 and the second line 312 may be visually separated. This will be described below.

Subsequently, the system analyzes only the first line 310 of the lines 310 and 312, thereby measuring irregularity of the glass substrate 200. Since the first line 310 and the second line 312 are clearly separated, it is easy for the system to obtain only information concerning the first line 310.

In brief, the system for measuring irregularity of the glass substrate of the present embodiment separates clearly the first line 310 corresponding to the first reflection light 212 from the second line 312 corresponding to the second reflection light 214 so as to measure accurately irregularity of the glass substrate 200, and then measures irregularity of the glass substrate 200 using only the first line 310.

Hereinafter, a method of separating the first line 310 and the second line 312 and various methods of measuring irregularity will be described in detail with reference to accompanying drawings.

Figure 4:
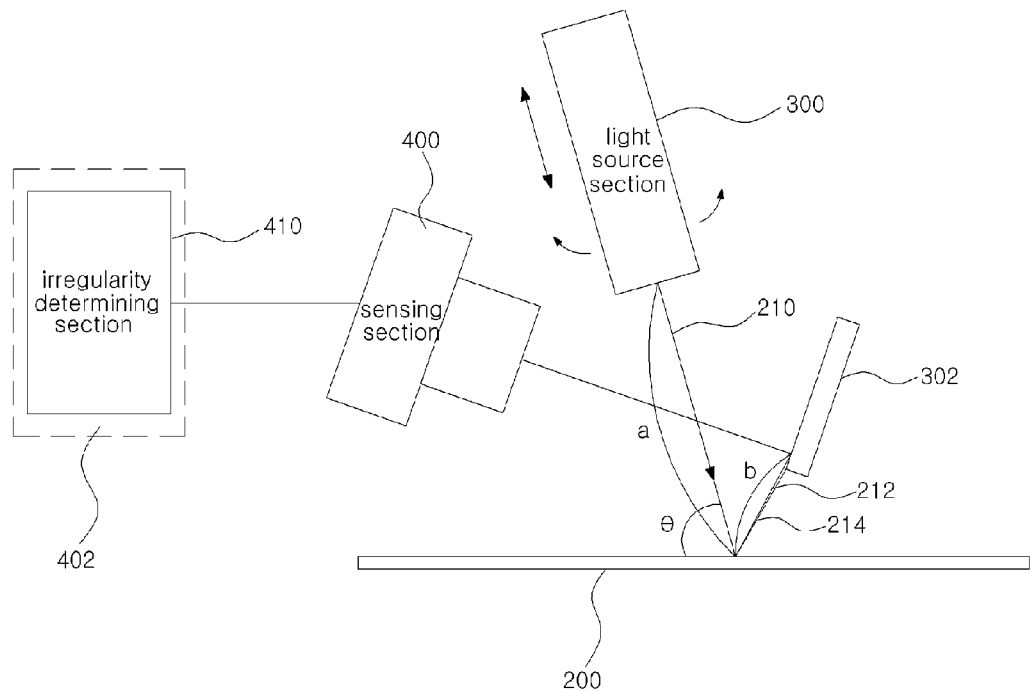
FIG. 4 is a view illustrating the system for measuring irregularity of the glass substrate in FIG. 3.
Figure 5:
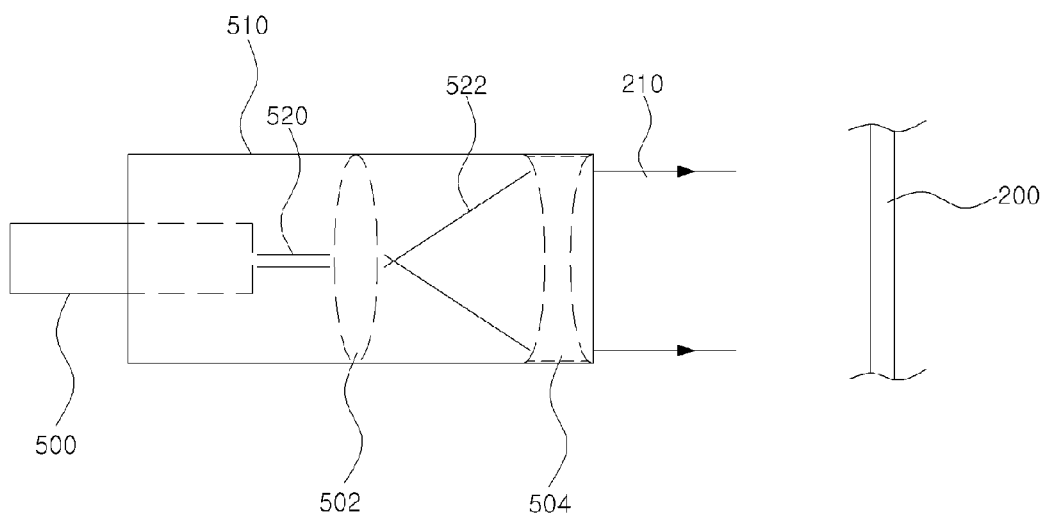
FIG. 5 is a view illustrating a light source section according to one example embodiment of the present invention.
Figure 6:
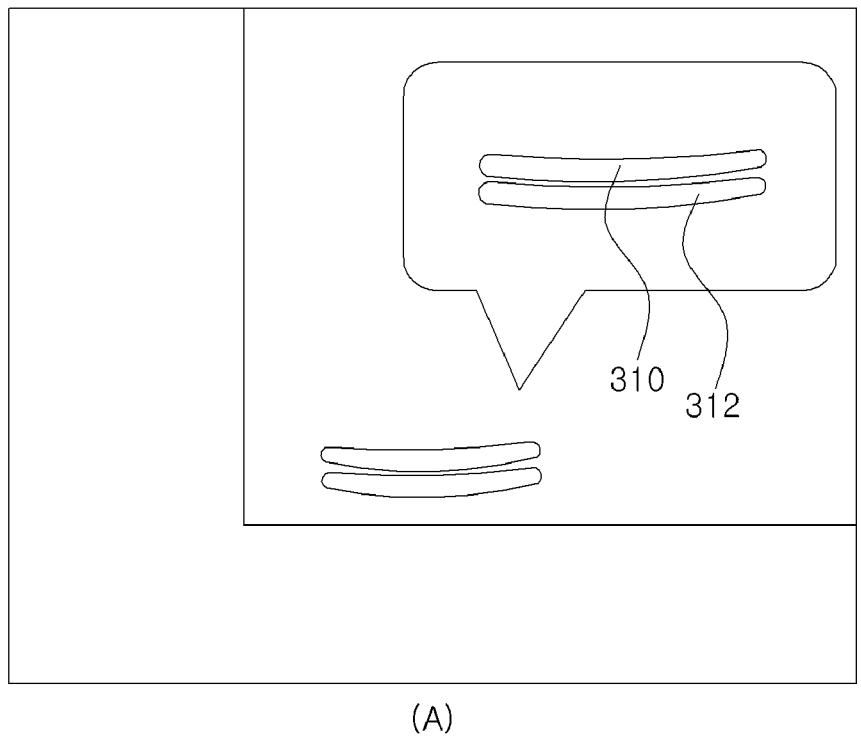
FIG. 6 is a view illustrating line pattern.
Figure 6:
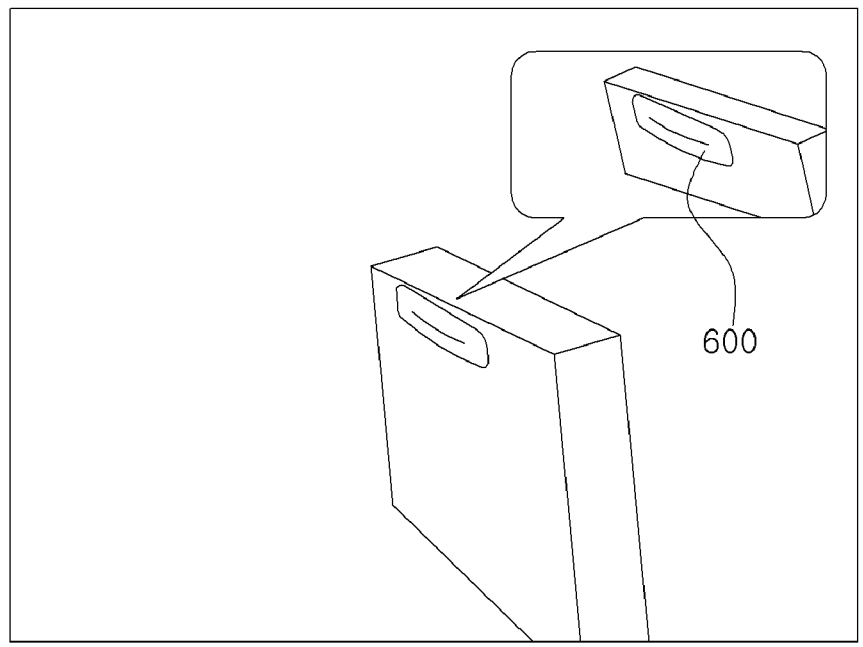

FIG. 4 is a view illustrating the system for measuring irregularity of the glass substrate in FIG. 3, and FIG. 5 is a view illustrating a light source section according to one example embodiment of the present invention. FIG. 6 is a view illustrating line pattern.

In FIG. 4, the system for measuring irregularity of the glass substrate of the present embodiment includes the light source section 300, the screen 302, a sensing section 400 and an irregularity measuring section 402.

The light source section 300 outputs a light having specific wavelength, and inputs e.g. the first light 210 as visible ray having constant beam width into the glass substrate 200.

In one embodiment of the present invention, the light source section 300 may include a light source 500, a first lens 502 and a second lens 504 as shown in FIG. 5.

The light source 500 is for example a laser using a light emitting diode, and outputs visible ray, ultraviolet ray or infrared ray.

The first lens 502 diffuses a light 520 outputted from the light source 500, and the second lens 504 changes the diffused light 522 into the first light 210 having constant beam width. Here, the second lens 504 may be a cylindrical lens.

That is, the light source section 300 may output the first light 210 having constant beam width.

In one embodiment of the present invention, the light source 500, the first lens 502 and the second lens 504 as elements of the light source section 300 may be included in one case 510 as shown in FIG. 5. Here, the elements 500, 502 and 504 in the light source section 300 are not controlled individually but are controlled to move in one body after the elements 500, 502 and 504 are set in the case 510. The case 510 may move up and down-right and left.

The light source section 300 is set with certain angle (angle θ 1 between the surface of the glass substrate 200 and the light source section 300) and a space distance a on the basis of the glass substrate 200 as shown in FIG. 4.

In one embodiment of the present invention, at least one of the angle θ 1 and the space distance a may vary to separate the lines 310 and 312 as described below. This will be described below.

Images corresponding to the reflection lights 212 and 214, i.e. lines 310 and 312 are formed on the screen 302. The screen 302 is disposed with spaced by certain distance b from the glass substrate 200.

The sensing section 400 senses the lines 310 and 312 formed on the screen 302, e.g. taking the lines 310 and 312 using a camera to obtain an image. Here, location and direction of the sensing section 400 are not limited as long as the sensing section 400 obtains the image of the lines 310 and 312 formed on the screen 302.

In another embodiment of the present invention, the sensing section 400 may obtain an image of only the first line 310 of the lines 310 and 312 formed on the screen 302. Since it is easy to extract only information concerning the first line 310 from the image of the lines 310 and 312 than to obtain and analyze the image of only the first line 310, it is desirable to obtain the image of the lines 310 and 312.

The irregularity measuring section 402 measures irregularity of the glass substrate 200 through analysis of the first line 310, and includes an irregularity determining section 410.

Particularly, the irregularity determining section 410 is connected to the sensing section 400 through wire or wireless communication, receives the image of the lines 310 and 312 from the sensing section 400, and extracts only the information concerning the first line 310 from the image. Here, since the first line 310 is scattering pattern and includes information concerning defect of the glass substrate 200, the irregularity determining section 410 may measure the irregularity of the glass substrate 200 through analysis of the first line 310.

The irregularity measuring section 402 may be realized as a computer (not shown), and may further include a display section, etc. so as to provide the measured result to a manager.

In addition, the computer may not only measure the irregularity but also control movement of the light source section 300 and the screen 302.

In short, the system for measuring irregularity of the glass substrate of the present embodiment obtains the image of the separated lines 310 and 312 and analyzes only the first line 310 of the image, thereby measuring accurately the irregularity of the glass substrate 200.

As described above, it is necessary to separate clearly the lines 310 and 312 so as to measure accurately the irregularity of the glass substrate 200. Accordingly, the system of the present embodiment sets properly the angle θ 1 between the glass substrate 200 and the light source section 300, the space distance a between the glass substrate 200 and the light source section 300, and the distance b between the glass substrate 200 and the screen 302 in order to obtain the separated lines 310 and 312.

Hereinafter, a process of setting the system will be described in detail through real experimental result.

The angle θ 1 between the light source section 300 and the glass substrate 200 and the space distance a were set to 45° and 110 mm, respectively. Then, a manager observed the lines 310 and 312 formed on the screen 302 with varying the distance b between the glass substrate 200 and the screen 302.

It is verified through the experiment that optimal distance b at which the lines 310 and 312 are visually separated as shown in FIG. 6(A) is 52 mm, and the lines 310 and 312 are separated without interfered until the distance b of approximately 60 mm. However, in case that the distance b is greater than 60 mm, the lines 310 and 312 are not separated clearly as shown in FIG. 6(B) and are interfered each other.

Subsequently, the angle θ 1 between the light source section 300 and the glass substrate 200 was set in sequence to 60°, 75° and 85° under the condition that the distance a between the light source section 300 and the glass substrate 200 maintains 110 mm. Then, the manager observed the lines 310 and 312 formed on the screen 302 with varying the distance b between the glass substrate 200 and the screen 302.

It is verified through the experiment that optimal distance b at which the lines 310 and 312 are clearly separated is 50 mm, 38 mm and 5 mm, respectively.

Then, the distance a between the light source section 300 and the glass substrate 200 was set in sequence under the condition that the angle θ 1 between the light source section 300 and the glass substrate 200 maintains constantly. Then, the manager observed the lines 310 and 312 formed on the screen 302 with varying the distance b between the glass substrate 200 and the screen 302.

As described above, the manager observed the lines 310 and 312 with varying variously the angle θ 1, the distance a and the distance b.

Briefly, the lines 310 and 312 are visually separated on the screen 302 in case that the distance b between the glass substrate 200 and the screen 302 is below approximately 60 mm under the condition that the angel θ 1 between the light source section 300 and the glass substrate 200 and the distance a between the light source section 300 and the glass substrate 200 are approximately 45° to approximately 80°, about 60 mm to about 120 mm. However, it is desirable that the screen 302 is spaced by minimum above 5 mm from the glass substrate 200 so as to prevent breakdown of the glass substrate 200, e.g. the distance b between the glass substrate 200 and the screen 302 is approximately 5 mm to approximately 60 mm.

Additionally, it is verified that the lines 310 and 312 are visually separated on the screen 302 in case that ratio of the distance a between the light source section 300 and the glass substrate 200 and the distance b to a part on which the first line 310 is formed of the screen 302 from the glass substrate 200 is 1:1 to 1:0.5 and the angle θ 1 between the light source section 300 and the glass substrate 200 is 45° to 80°.

Furthermore, it is verified that the lines 310 and 312 are visually separated on the screen 302 in case that the distance b between the glass substrate 200 and the screen 302 decreases according as the angle θ 1 between the light source section 300 and the glass substrate 200 increases.

Hereinafter, a process of setting the system for measuring irregularity of the glass substrate of the present embodiment will be described in detail.

Firstly, the light source section 300 and the screen 302 are established at specific location with specific angle based on the glass substrate 200.

Subsequently, the system for measuring irregularity has moved the light source section 300 up and down-right and left until the lines 310 and 312 are clearly separated. That is, the system detects optimal angle θ 1 and the distance a at which the lines 310 and 312 are clearly separated with varying the angle θ 1 and the distance a between the light source section 300 and the glass substrate 200. Here, movement of the light source section 300 may be automated in accordance with control of the manager.

Then, the system sets and fixes the light source section 300 at the detected distance a with the detected angle θ 1.

Subsequently, the system for measuring irregularity measures the irregularity of the glass substrates 200 with moving in sequence the glass substrates 200 using a roller.

In other words, the system for measuring irregularity may be realized through a method of adjusting the light source section 300 after setting the screen 302 at specific location.

In another embodiment of the present invention, the system for measuring irregularity may be realized through a method of adjusting the screen 302 under the condition of fixing the light source section 300.

Referring to FIG. 2 to FIG. 6, the system for measuring irregularity of the glass substrate of the present embodiment uses lens, and sets the light source section 300 and the screen 302 at proper location with proper angle on the basis of the glass substrate 200 to separate clearly the lines 310 and 312. Here, the process of adjusting the light source section 300 and the screen 302 may be manually performed by the manager, but be automatically performed by a computer.

Hereinafter, the method of measuring irregularity of the glass substrate of the present embodiment will be compared with a conventional method of measuring irregularity of the glass substrate.

The convention system uses a method of coating specific substance on a lower surface of the glass substrate or a method of floating the glass substrate on water, etc. so that a light inputted into the glass substrate is not reflected by the lower surface of the glass substrate. Accordingly, the conventional system should perform further a process of removing the substance coated on the lower surface of the glass substrate, etc. after measuring the irregularity of the glass substrate. As a result, time and cost taken for measuring the irregularity of the glass substrate may increase, and yield of the display device using the glass substrate may be lowered.

However, the system of the present invention does not perform any process to the lower surface of the glass substrate 200 but uses the glass substrate 200 in itself, and is realized so that the lines 310 and 312 formed on the screen 302 are separated. Accordingly, the system does not need additional process, and so time and cost taken for measuring the irregularity may be reduced and yield of the display device using the glass substrate 200 may be enhanced.

Additionally, since the system for measuring irregularity is realized with simple elements 300, 302 and 400, it is easy to realize the system and error generation possibility of the system is little.

Figure 7:
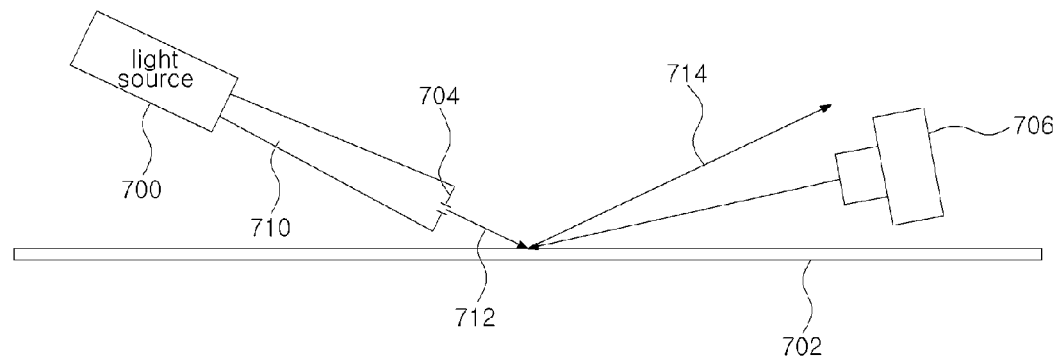
FIG. 7 is a view illustrating a system for measuring irregularity of a glass substrate according to a second embodiment of the present invention.
Figure 8:
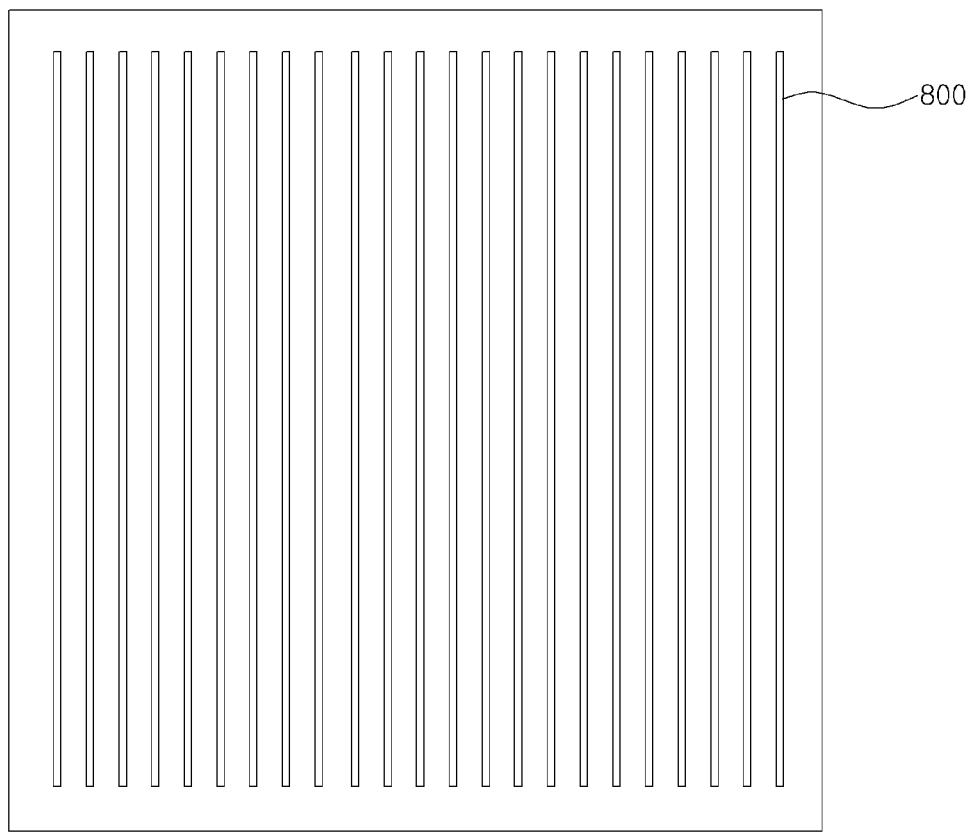
FIG. 8 is a view illustrating a slit section according to one example embodiment of the present invention.
Figure 9:
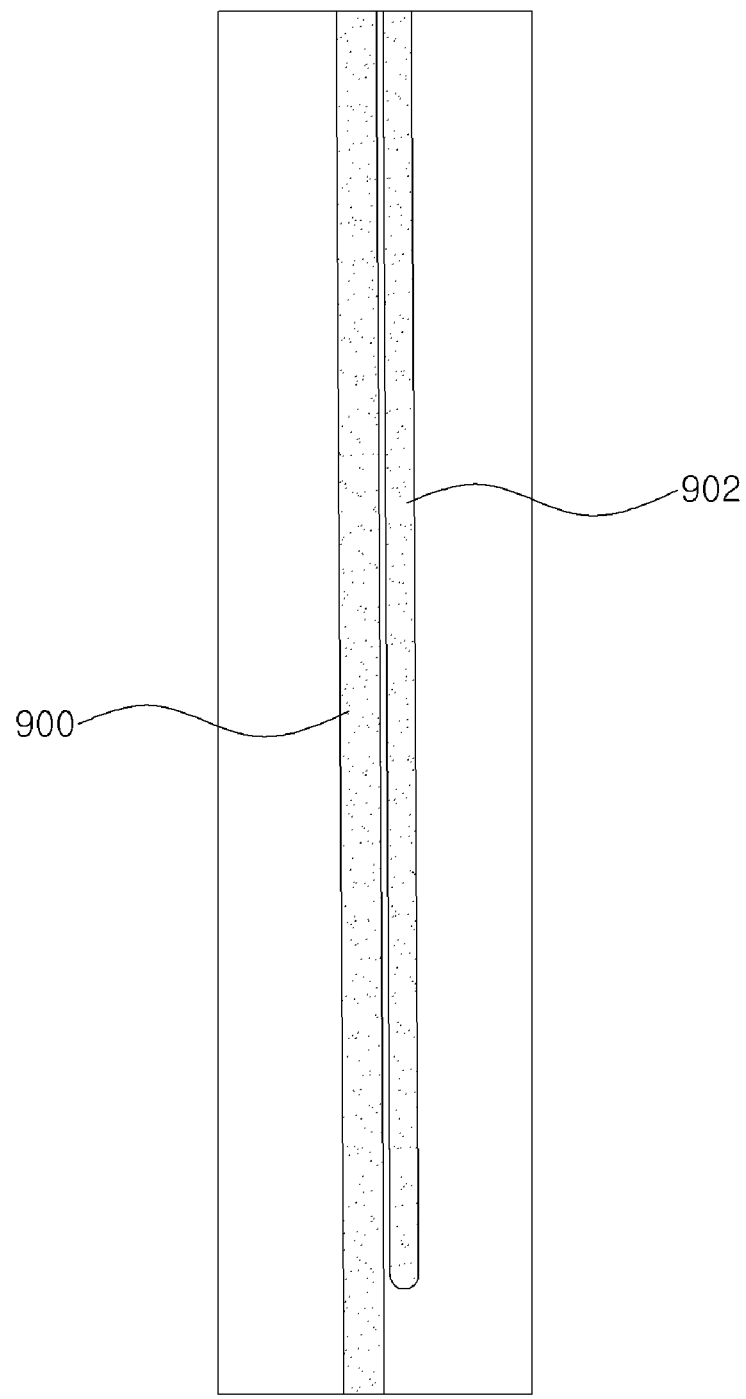
FIG. 9 is a view illustrating sensing result in the system in FIG. 7.

FIG. 7 is a view illustrating a system for measuring irregularity of a glass substrate according to a second embodiment of the present invention, and FIG. 8 is a view illustrating a slit section according to one example embodiment of the present invention. FIG. 9 is a view illustrating sensing result in the system in FIG. 7.

In FIG. 7, the system for measuring irregularity of the glass substrate of the present embodiment includes a light source 700, a slit section 704 and a sensing section 706.

The light source 700 outputs a first light 710 having specific wavelength and is for example a laser.

The slit section 704 includes at least one slit 800 as shown in FIG. 8, and opens a part or whole of the slits 800 when the irregularity is measured. As a result, the first light 710 outputted from the light source 700 is changed into a second light 712 having constant beam width according as the first light 710 propagates through the slit 800.

The second light 712 is inputted into a glass substrate 702 and then is reflected by an upper surface and a lower surface of the glass substrate 702.

The sensing section 706 senses the upper surface of the glass substrate 702, e.g. takes the upper surface unlike the first embodiment where the sensing section 400 senses the screen 302, thereby obtaining an image in which two lines 900 and 902 are shown as shown in FIG. 9. Here, the first line 900 is interference fringe corresponding to a first reflection light reflected by the upper surface of the glass substrate 702, and the second line 902 is interference fringe corresponding to a second reflection light reflected by the lower surface of the glass substrate 702.

The image sensed by the sensing section 706 is provided to an irregularity determining section (not shown), and the irregularity determining section measures the irregularity of the glass substrate 702 by analyzing only the first line 900 of the lines 900 and 902.

In brief, the system for measuring irregularity of the glass substrate of the present embodiment uses the slit section 704. Moreover, the sensing section 706 takes directly the glass substrate 702, thereby obtaining the image of the lines 900 and 902.

The lines 900 and 902 may be clearly separated or interfered in accordance with location of the slit section 704, which is not described above. Accordingly, the system of the present embodiment is set through a method of adjusting location f the slit section 704 or the light source 700 so that the lines 900 and 902 may be clearly separated. Then, the system measures in sequence irregularity of the glass substrates 702 moving through a roller.

Figure 10:
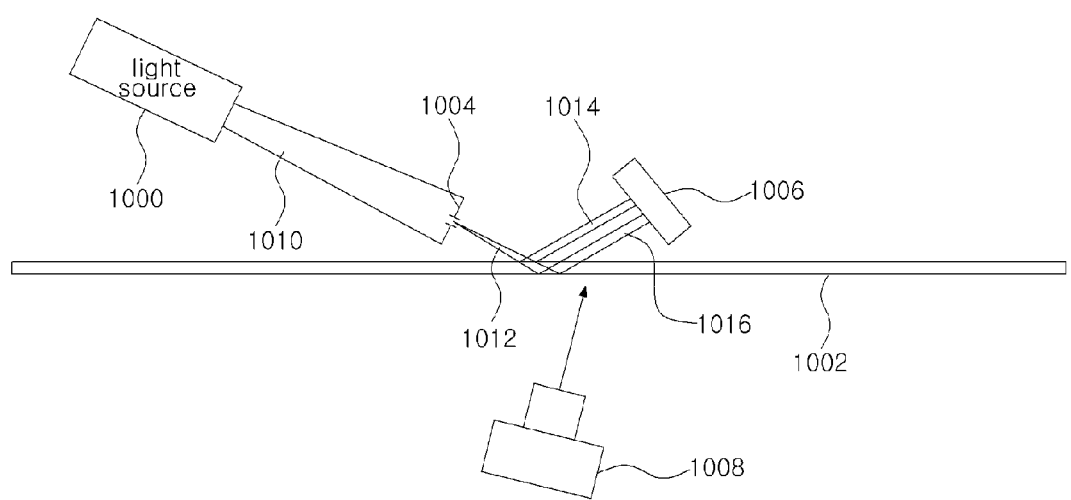
FIG. 10 is a view illustrating a system for measuring irregularity of a glass substrate according to a third embodiment of the present invention.

FIG. 10 is a view illustrating a system for measuring irregularity of a glass substrate according to a third embodiment of the present invention.

In FIG. 10, the system for measuring irregularity of the glass substrate of the present embodiment includes a light source 1000, a slit section 1004, a screen 1006 and a sensing section 1008.

Unlike the second embodiment where the sensing section 706 senses directly the glass substrate 702, the system of the present embodiment uses the slit section 1004, and measures irregularity of the glass substrate 1002 by sensing lines corresponding to reflection lights 1014 and 1016 formed on the screen 1006.

On the other hand, the sensing section 1008 may be located under a lower surface of the glass substrate 1002 unlike the other embodiments. However, the sensing section 1008 may be located on the glass substrate 1002 in accordance with set angle of the screen 1006.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A system for measuring irregularity of a glass substrate comprising:
    a light source section configured to output a first light to the glass substrate;
    a screen; and
    an irregularity measuring section,
    wherein the first light outputted from the light source section is reflected by an upper surface and a lower surface of the glass substrate, a first reflection light reflected by the upper surface of the glass substrate is inputted into the screen, a first line is formed on the screen in accordance with the input of the first reflection light, a second reflection light reflected by the lower surface of the glass substrate is inputted into the screen through the upper surface, a second line is formed on the screen in accordance with the input of the second reflection light, and the light source section and the screen are disposed on the basis of the glass substrate so that the lines are separated, and the irregularity measuring section measures irregularity of the glass substrate using only the first line of the lines formed on the screen.

2. The system of claim 1, further comprising:
    a sensing section configured to sense the lines formed on the screen; and
    wherein the irregularity measuring section is configured to extract only the first lines of the lines sensed by the sensing section and measure irregularity of the glass substrate by analyzing the extracted first line.

3. The system of claim 1, wherein the light source section includes:
    a light source configured to output a second light;
    a first lens configured to diffuse the second light outputted from the light source; and
    a second lens configured to change the second light diffused by the first lens into the first light having constant beam width.

4. The system of claim 3, wherein the light source, the first lens and the second lens are included in one case, and the case moves omnidirectionally,
    and wherein the system detects optimal location at which the lines are separated through a method of moving the case under the condition of fixing the glass substrate and the screen, and fixes the case at the detected location.

5. The system of claim 4, wherein ratio of distance between the light source section and the glass substrate and distance to a part on which the first line is formed of the screen from the glass substrate is approximately 1:1 to approximately 1:0.5 and the light source section locates in the range of about 45° to about 80° on the basis of the glass substrate.

6. The system of claim 4, wherein the lines are separated in case that distance to a part on which the first line is formed of the screen from the glass substrate is less than approximately 60 mm under the condition that distance between the light source section and the glass substrate is about 60 mm to about 120 mm and the light source section locates in the range of approximately 45° to approximately 80° on the basis of the glass substrate.

7. The system of claim 4, wherein distance between the glass substrate and the screen decreases according as angle between the glass substrate and the light source section increases under the condition that distance between the second lens and the glass substrate fixes.

8. A system for measuring irregularity of a glass substrate comprising:
    a light source configured to output a light; and
    a slit section configured to have at least one slit; and
    an irregularity measuring section,
    wherein the light outputted from the light source is inputted into the glass substrate through the slit of the slit section, the inputted light is reflected by an upper surface and a lower surface of the glass substrate, and a first line corresponding to a first reflection light reflected by the upper surface of the glass substrate is separated from a second line corresponding to a second reflection light reflected by the lower surface of the glass substrate, and the irregularity measuring section measures irregularity of the glass substrate using only the first line of the lines.

9. The system of claim 8, further comprising:
    a sensing section configured to sense the first line and the second line; and
    wherein the irregularity measuring section is configured to extract only the first line of the lines sensed by the sensing section and measure irregularity of the glass substrate by analyzing the extracted first line, and the sensing section senses the lines by taking directly the glass substrate.

10. The system of claim 8, further comprising:
    a screen in which the first reflection light and the second reflection light are inputted; and
    a sensing section;
    wherein the first line corresponding to the first reflection light and the second line corresponding to the second reflection light are formed on the screen, the sensing section senses the lines, and the irregularity measuring section measures irregularity of the glass substrate by extracting and analyzing only the first line of the lines sensed by the sensing section.

11. A method of measuring irregularity of a glass substrate, the method comprising:
    inputting a first light into the glass substrate; and
    sensing at least one of a first line corresponding to a first reflection light reflected by an upper surface of the glass substrate and a second line corresponding to a second reflection light reflected by a lower surface of the glass substrate, the second reflection light being outputted through the upper surface,
    wherein the first line and the second line are separated, and the irregularity of the glass substrate is measured by using only the first line of the lines.

12. The method of claim 11, further comprising:
    extracting only the first line from the lines.

13. The method of claim 12, wherein the step of inputting the first light into the glass substrate includes:

diffusing a second light using a first lens; and changing the diffused second light into the first light having constant beam width using a second lens, and inputting the first light into the glass substrate, wherein the first line is formed on a screen by the first reflection light reflected by the upper surface of the glass substrate, and the second line is formed on the screen by the second reflection light reflected by the lower surface of the glass substrate.

14. The method of claim 13, wherein the light source, the first lens and the second lens are included in one case, the case moves omnidirectionally, and the method further comprising:

moving the case until the lines are separated under the condition of fixing the glass substrate and the screen; and fixing the case after the lines are separated, and wherein the irregularity of the glass substrate is measured under the condition that the light source and the screen are fixed.

15. The method of claim 13, wherein ratio of distance between the second lens and the glass substrate and distance to a part on which the first line is formed of the screen from the glass substrate is approximately 1:1 to approximately 1:0.5 and the light source locates in the range of about 45° to about 80° on the basis of the upper surface of the glass substrate.

16. The method of claim 13, wherein the lines are separated in case that distance to a part on which the first line is formed of the screen from the glass substrate is less than approximately 60 mm under the condition that distance between the second lens and the glass substrate is about 60 mm to about 120 mm and the light source locates in the range of approximately 45° to approximately 80° on the basis of the upper surface of the glass substrate.

17. The method of claim 12, wherein the step of sensing includes:

sensing the first line and the second line by taking directly the glass substrate, and wherein the first light is inputted into the glass substrate through a slit section having at least one slit.

18. The method of claim 12, wherein the first reflection light is inputted to a screen, the first line is formed on the screen by the first reflection light, the second reflection light is inputted to the screen, and the second line is formed on the screen by the second reflection light, and wherein the first light is inputted to the glass substrate through a slit section having at least one slit.

* * * * *